(12) United States Patent
Huang et al.

(10) Patent No.: US 6,488,716 B1
(45) Date of Patent: Dec. 3, 2002

(54) ANATOMIC FEMORAL PROSTHESIS FOR TOTAL HIP ARTHROPLASTY

(76) Inventors: Guofu Huang, 23-108 Honglou Li Longchang Rd, Tianjin (CN), 300211; Xue Li, 54 Jaqui Ave., Morris Plains, NJ (US) 07950

( * ) Notice: Subject to any disclaimer, the term of this patent is extended or adjusted under 35 U.S.C. 154(b) by 0 days.

(21) Appl. No.: 09/364,420

(22) Filed: Jul. 30, 1999

(51) Int. Cl.[7] ................................................. A61F 2/32
(52) U.S. Cl. ................................................. 623/23.12
(58) Field of Search ......................... 623/23.11, 23.12, 623/23.13, 23.14, 23.15

(56) References Cited

U.S. PATENT DOCUMENTS

| | | | |
|---|---|---|---|
| 4,550,448 A | | 11/1985 | Kenna |
| 4,846,841 A | | 7/1989 | Indong |
| 4,976,740 A | * | 12/1990 | Kleiner ................... 623/23.14 |
| 5,004,476 A | | 4/1991 | Cook |
| 5,007,935 A | * | 4/1991 | Vincent et al. ......... 623/23.14 |
| 5,133,769 A | | 7/1992 | Wagner |
| 5,725,593 A | | 3/1998 | Caracciolo |

FOREIGN PATENT DOCUMENTS

| | | |
|---|---|---|
| CN | 98200233.5 | 1/1998 |

OTHER PUBLICATIONS

Gerald A.M. Finerman etc. Total Hip Arthroplasty Outcomes. 1998.

Lars Carlson Femoral Neck Retention in Hip Arthroplasty; Acta Orthop Scand (1998) 59 (1) 6–8.

O. S. Imura Hip Mechanics; 1993.

M. A. Freeman. Why Reset the Neck? J. Bone Joint Surg. (1986) 68–B 346–349.

Paul G.J. Maquet Biomechanics of the hip. 1985.

* cited by examiner

*Primary Examiner*—David J. Isabella

(57) ABSTRACT

An anatomic, neck-locking femoral prosthesis for use in total hip replacement is described. The asymmetric device fundamentally comprises a shell with a hollow bell-shape, which is anchored on the outside of retention neck and the trochantic bed of the femur. The prosthesis is mechanically fastened during the operation and further biologically secured by in-growing bone around the neck and trochantic bed area through the side holes on the shell and by growing into its interior porous coating surface of implant thereafter. The loading force on the femoral head would be well distributed on the shell and directly conducted into the cortex bone of the femoral shaft through the shell. The prosthesis would provide a simple and safe replacement method of hip prosthesis for most patients, particularly benefit for younger patient who has a defective head of femur. Because of less changes in term of anatomic structure of femur, new device could eliminate most of side effects and complications, which appear in regular stem type prosthesis of THA and thereafter.

8 Claims, 5 Drawing Sheets

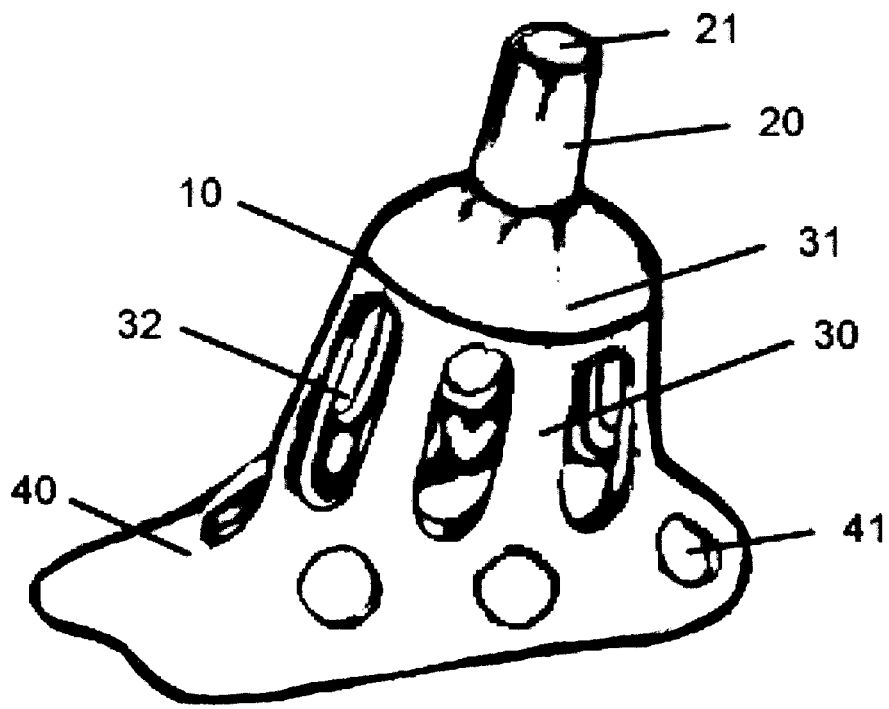
Figure 1. An anterior side view of a left femoral prosthesis.
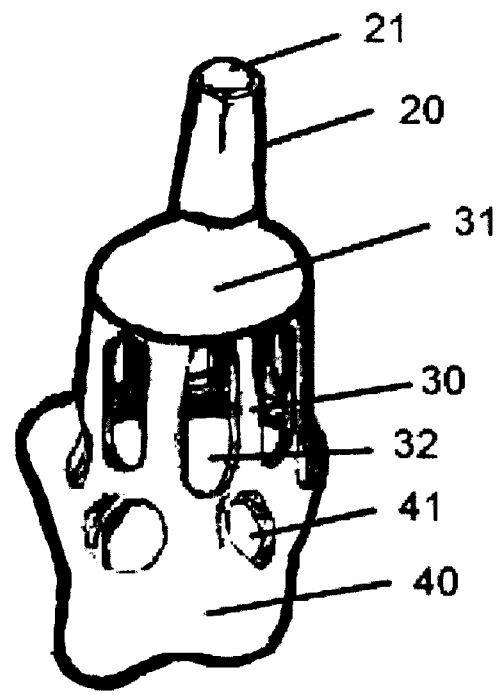
Figure 2 An isometric view of the shell (medial side).

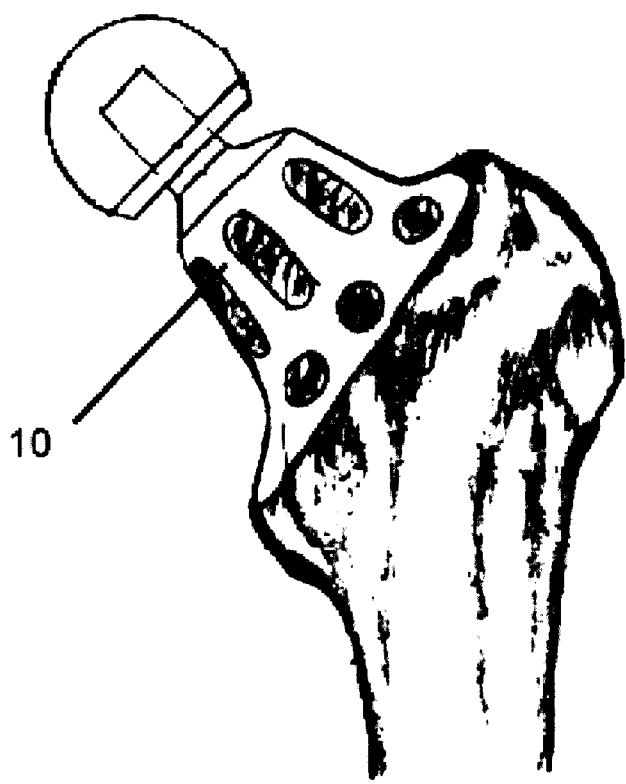
Figure 3  An anterior view of the hollow shell implanted on femoral shaft.

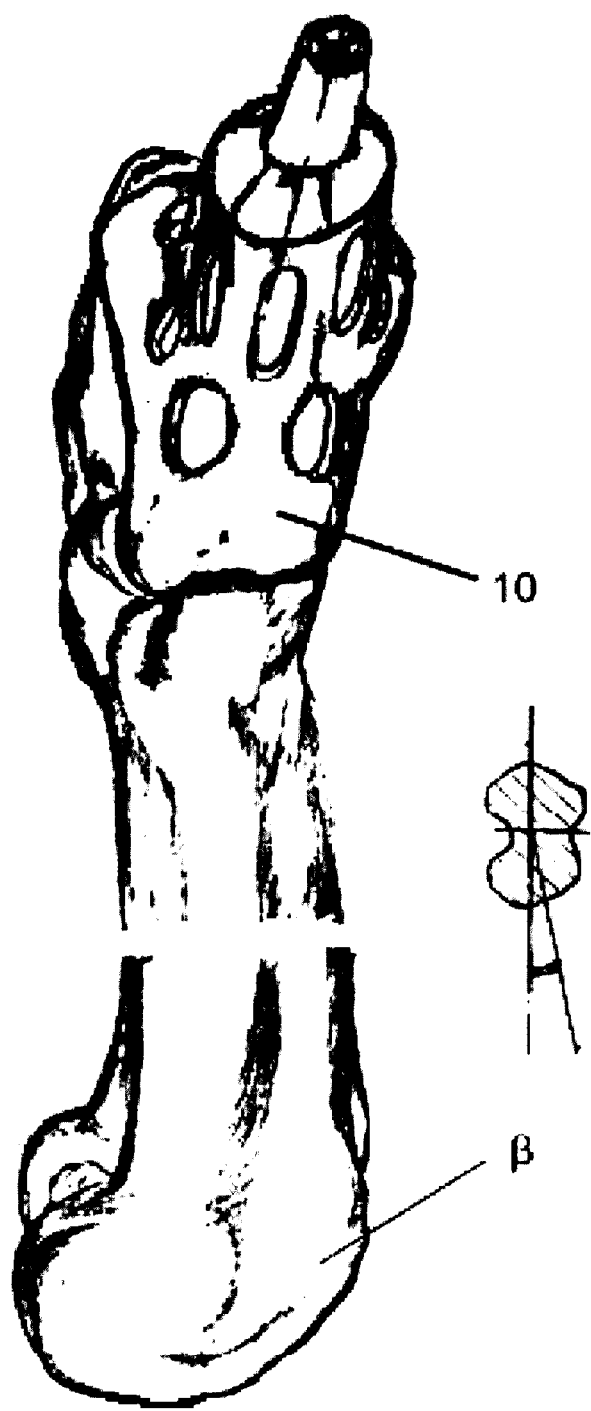
Figure 4. A medial view of the hollow shell implanted on femoral shaft.

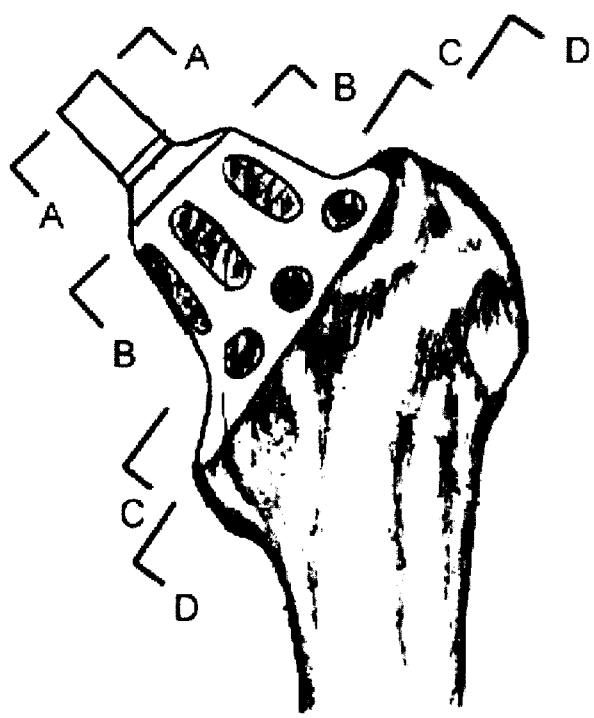
Figure 5. An anterior view of the hollow shell implanted; illustrating several transverse cross-sections A--A through D-D.

Figure 6. A transverse cross section of A-A level of the hollow shell.
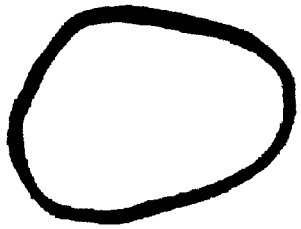
Figure 7. A transverse cross section of B-B level of the hollow shell.
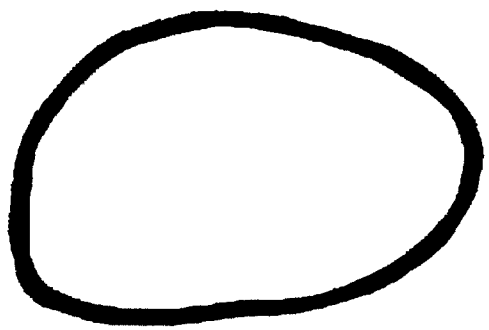
Figure 8. A transverse cross section of C-C level of the hollow shell.
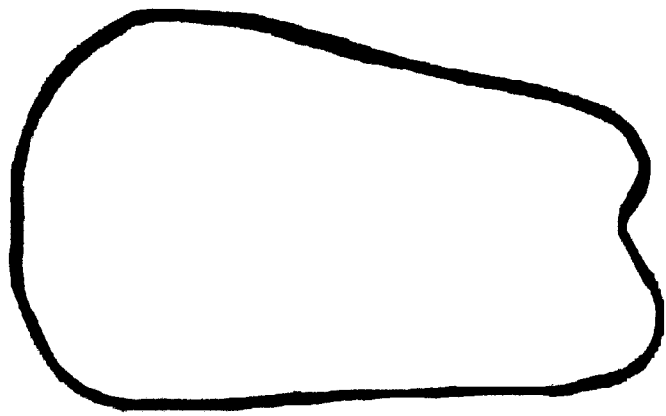
Figure 9. A transverse cross section of D-D level of the hollow shell.

ANATOMIC FEMORAL PROSTHESIS FOR TOTAL HIP ARTHROPLASTY

BACKGROUND OF THE INVENTION

1. Field of the Invention

The present invention relates to a femoral prosthesis to be applied in total hip arthroplasty (THA). More specifically, new femoral prosthesis is a necklocking femoral component. It is anchored on the outside of retention neck and the trochantic bed of the femur and mechanically fastened during the operation.

2. Description of the Prior Art

The human hip joint comprises a socket or an acetabulum and a ball or femoral head. The femoral head is attached to the femur through a neck with reduced diameter and is received within the acetabulum for universal pivotal movement. In natural femur, most of loading force of hip is located on the head and distributed through the hard cortex of the femoral neck. It would be further conducted to the femur cortical bone and the joint of knee. If the femoral head becomes diseased or damaged, it can be replaced with a prosthetic femoral component. About 40 years ago, Prof. Sir John Chamley started a revolution in total hip replacement, a stem hip prosthesis. THA has been a tremendously successful surgical invention for patients with disabling arthritis of the hip. Quality of life is predictably improved following THA.

The implantable hip prostheses used comprise, in basic design, one or two piece(s) including a replacement head and femoral neck attached to an elongated metal stem that is adapted for receipt in a cavity formed in the proximal region of the femur. In practice of THA, the natural femoral head and neck has been completely removed, in order to open a canal on the proximal femur. In that model, most of compression force applied on the prosthetic femoral head would be directly conducted into the intramedullar canal of the proximal femur. Most of them are concentrated on the certain local area of the canal. Various patents of THA have been issued around this idea during past 30–40 years. Most of them have been fused on an improvement on shape of the stem for accurately fitting into intramedullar canal of shaft and a method to form a stable, longlasting prosthesis.

In early prior art, the stem of prosthesis was cemented within the femoral medullar cavity by use of a plastic cement, such as PMMA. After decades of practice, there were several infirmities associated with this kind of prosthesis installation. Typically, the cement would be deteriorated with age. In the meanwhile, the constant cyclic loading applied to the stem of the prosthesis by the action of simple walking causes cement to fracture and break loose from the femoral cavity, thereby requiring another operation to re-fix the prosthesis. Loosening of the cemented implants from canal was a common problem in THA and was being recorded with increasing frequency, leading eventually to the description of a condition called "cement disease". This "disease" seemed to be found with any of the nearly over 100 different prostheses in use, regardless of the size of the head, the shape of stem, the cementing technique used, or their modularity.

Because of problems associated with cementing a prosthesis hip within the femur, a cementless type of implant procedure had been developed and accepted by the orthopaedic community as a replacement. The cementless hip prosthesis includes a porous coating surface or coating materials, called hydroxyapatite (HA), over the length of the stem, such that natural growing bone after surgery penetrates into the porous surface or HA of the stem, thereby firmly fixing, at least in theory, the femoral stem within the femoral cavity. In general, such procedure requires that the patient would be relatively immobile for a number of weeks following the surgery, in order to allow the bone growth occur and thereafter restrict his physical activity until a firm bound is created. The period of time may involve a full twelve months. Secondly, micro-motion of the implant cannot be avoided in the immediate and early stages after surgery, which, more or less, causes the position or orientation changes of implanted prosthesis. The outcomes from such procedure would be largely depended upon the condition of patient in term of their health condition during the surgery period and activities thereafter. Even that, in best case, this procedure can not completely avoid problems that happened in the cement procedure. In addition, it becomes very difficult to remove a firmly bonded prosthesis, if a failure of prosthesis occurs after surgery. Another downside associated with existing devices and procedures is that, in order to avoid the loosening prosthesis, in prior art, the device has to be as much as perfectly fit into the medullar cavity in term of its orientation, position and the deepness at the medullar canal. From point of view of doctor, they have to spend most time during the surgery to carefully remove bone, which mostly is healthy and functioning, and open a canal in the cancellous bone in term of the precise position, shape and size of canal. It is a time consuming and skilful part in the operation. In fact, for most patients, who needs total hip replacement, their natural neck is functioning and is still in a good shape.

In addition, because design of the stem type devices and its operating procedure of THA would partially alter the structure and functions of the natural femoral system, somehow such surgery would make a damage on proximal femur and affect the growth of bone as well as quality of intact bone. In general, this procedure could not be recommended for young patients (younger than 50 years old), who has a damage on its femoral head, because of concerns about both durability of the prosthesis and most of side-effects and complications appeared in the regular stem type prosthesis, which could lead a need for multiple revisions in their lifetime.

Several previous studies have discovered that major reasons for the vertical migration and subsidence of the femoral component in hip replacement, which causes a likelihood loosening of the device, accurately, are: 1) From point of view of material properties, the cancellous bone is very different from one of cortical bone and metal. For example, the elastic modulus of the cortical bone, cancellous bone and stem (CoCrMo) are $17.3 \times 10^9$, $324.6 \times 10^6$ and $196 \times 10^9$ (Pa), respectively. In principle, function of the cancellous bone is not for supporting any load at all. Once the cancellous bone contact with hard surface of metal stem and is being loaded with force beyond its physiological limits, the plastic deformation happened, which would accumulate over extended period of time and manifest itself as migration of the prosthesis. 2) There are a change and difference on model of the force loading and distribution on the proximal portion of the femur between the intact femur and implanted stem prosthesis. According to Wolff's law, changes in stress distribution through a bone eventually cause definite alteration in its internal structure. For example, the strain applied on femoral head is transferred along the length of the stem and compression force from femoral head is only focused on a small and local area of the medullas channel, which leads a local plastic deformation of the cancellous bone. 3) The current surgery of THA has generally required removal of entire head and neck portion as well as some hard outer cortical bone, in order to open the intramedullar canal and install the prosthesis. Such surgery causes a lot of anatomical changes on natural system, in term of blood circulation and supply to this area, so that it also leads further physical changes in proximal femur with respect of the bone quality after surgery. Those problems have been recognised for quite some time by orthopaedic community. Obviously, the fact of that problems are associated with the current design of the hip prosthesis, such as aseptic loosening, fatigue fracture, postoperative infection and stress shielding, could directly or indirectly relate to the stem-style design of the prosthesis with respect of the weakness on both biomechanical and physiological outcomes from the existing THA.

There are also several patents of femoral prostheses issued, which have non-stem construction of femoral prosthesis and intended to retain the femoral neck. Most of them focus only on the replacement of the defective femoral head, which eliminates overcutting healthy bone from patient. For example, U.S. Pat. No. 5,133,769 (Wagner) teaches the cap for a femoral head, which can be imbedded without the use of cement. U.S. Pat. No. 4,976,740 (Kleiner) describes an anchored femoral dome that can be abutted with a sculpted femoral head through mechanical fastens. U.S. Pat. No. 5,725,593 (Caracciolo) describes a total anatomic hip prosthesis which applied a cap on the defective femoral head with anchorage means fitting by pressure the acetabulum in the iliac fossa. Those technologies all have its limitation and might not be widely applied. Because the size of femoral head varies a lot from patient to patient, it is difficult to have devices for matching each individual one. In most case, the femoral neck, more or less, has been damaged, so that it can not fully support the load from new head at all, even though the head has been repaired.

In point view of practice, beside diseased femoral head, most of the surface and the subsurface bone tissue around proximal femur is actually healthy, particularly neck portion of femur for many case. In these situations, it is undesirable to remove the healthy portion of the femoral neck. It has been recognised in previous studies that the femoral neck, particularly the medial neck cortex of femur, plays a very important role in both loading and conducting compression force on proximal femur. Thus, the retention of the femoral neck and conducting the load through cortical bone of femur would be a very important strategy for designing a new prosthesis hip and developing a new procedure of its implantation.

SUMMARY OF THE INVENTION

In light of foregoing problems with prior art, particularly, of the stem-type femoral components and procedures, it is an object of the present invention to provide a new anatomic, neck locking femoral component for THA, by which patient do not need the femoral neck removed anymore. A hollow neck-shell, which supports the prosthetic femoral head, would be anchored onto the outside of retention neck and the trochantic bed of the proximal femur after resecting the diseased or damaged head of femur. The shell is mechanically secured during operation and biologically fastened by in-growth bone surround the femoral neck during recovery period. It eliminates most of the complications from the installation of the existing stem-type hip prostheses.

Another object of present invention is to provide an ideal solution in both the biomechanical and physiological function to the replaced femur in the arthroplasty, in the respect of stress and strength distribution on both the implanted prosthesis and the structures of retention bone. The loading force would be well distributed on the shell and directly conducted into the cortex bone of the femoral shaft through the prosthetic hollow shell.

Still another object of the present invention is to provide an ideal manner to install femoral prosthesis into human body and to eliminate the damage and change on the natural structure of human body in term of its anatomic structure and its blood flow in the proximal area of femur. The level of the resection is just bellowing the level of the femoral head osteotomy. It is an ideal solution for younger (18 years old or up) patient, who has a damaged femoral head. Because of non-stem design of the femoral prosthesis, there are no any damages on intra-medullar canal and bone marrow of proximal femur. The new device would not obstruct the bone growing in young patient, in respect of the bone growth in both the medullar and shaft of femur.

Still another object of the present invention is provide a femoral prosthesis that allows a patient to be substantially completely mobile after the operation and needs a shorter recovery period, because of a simple operative technique and a shorter period of the operation time. Furthermore, such an implanted femoral prosthesis, if necessary, may be easily removed in a number of years following the initial surgery for another surgery.

BRIEF DESCRIPTION OF THE DRAWINGS

FIG. 1 is an anterior side view of a left femoral prosthesis.

FIG. 2 is an isometric view of a shell (medial side).

FIG. 3 is an anterior view of the hollow shell implanted on femoral shaft.

FIG. 4 is a medial view of the hollow shell implanted on femoral shaft.

FIG. 5 is an anterior view of the hollow shell implanted; illustrating several transverse cross-sections A—A through D—D.

FIG. 6 is a transverse cross section of A—A of the hollow shell.

FIG. 7 is a transverse cross section of B—B of the hollow shell.

FIG. 8 is a transverse cross section of C—C of the hollow shell.

FIG. 9 is a transverse cross section of D—D of the hollow shell.

DESCRIPTION OF THE PREFERRED EMBODIMENT

The present invention is directed to an asymmetric, neck-locking femoral prosthesis for implantation on the retention neck of the proximal femur. Referring to FIGS. 1, 2, in general, the necklocking shell (10) has a hollow bell shape with an asymmetric configuration for housing into either the left or right side of the retention neck and trochantic bed of the femur, respectively and a screw for attaching and securing the shell to femur. More particularly, certain aspects of the present invention are directed to a non-stem femoral prosthesis that comprises several key features that provide an optimum configuration of the following factors:

(a) A minimum removal of bone during implantation, particularly retaining the femoral neck and keep the intramedullar canal of shaft in functioning, which could avoid any side-effect associated with opening intramedullar canal of the shaft.

(b) A better contact and stability of the implant/bone interface and maximum ease of installation of the prosthesis.

(c) The loading force applied on the femur head is well distributed on the shell and is further conducted into the cortical bone through body of shell instead loading on cancellous bone of the femur through the stem.

Referring now to drawings, a preferred embodiment of left femoral neck-locking component is illustrated in FIG. 1. It should be noted that, while the description of the invention and the related figures are directed the left femoral component, the present invention is also applicable to a right femoral component, which is merely a mirror image of the left component described and illustrated herein.

In general, the diseased or fractured femoral head can be resected at the level bellow the head, most preferably a resection is just bellow the head. The intact neck and the tronchantic bed of femur could be sculpted by ancillary equipment (not shown). The hollow shell would be tightly anchored onto the outside of the retention neck and the trochantic bed of femur. An important feature of the overall design of implantation, which is discussed in greater detail bellow, is to allow for a higher retention of the femoral neck and global distribution of load to cortex bone of femur.

The construction of the hollow shell can be further divided into mainly three portions, according to its geometrical configuration: a proximal portion (20), a hollow cylinder portion (30) and a foot portion (40) of the shell.

Preferably, the proximal portion, tapered cone, (20) of the shell is a neck-shape for fitting into the socket of an articulation component that is a commercially available component. The artificial articulation usual is a metal ball connected to a cylinder with a socket at its bottom. A variation on the diameter of the ball and the length of the cylinder is effective to make adjustment in order to allow prosthesis fitting into each individual configuration of patient's femur. The neck substantially connects with the hollow cylinder (30) through a bow shape transmitter or shoulder (31). The center of neck defines a central longitudinal axis of the shell. The longitudinal axis of the shell forms an inclination angle from about 120 to about 145 degrees toward the longitudinal axis of femoral shaft (α in FIG. 3) and an anteversion angle from about 7 to about 15 degrees toward the plane of the body, sagittal plane (β in FIG. 4), if the prosthesis is implanted. For the preferred embodiment, they are 127 degrees and 8 degrees, respectively.

The preferred tapered cone neck is a flat-tipped cone with a height about 15 mm.

In the insider of the through hole (21) of the cone, there is a stage (not shown) for supporting a screw, which is about 9-mm depth from the upper edge of the cone.

There is a method of attaching the shell in alignment with longitudinal axis of the femoral neck. The screw, such as a self-tapping screw, is insertable through hole (21) of the tapered cone, engages with the shaft of femur along with the center of the cone (20) as well as the center of the femoral neck and shaft and secures the shell to the retention neck and the trochantic bed of femur.

The hollow cylinder (30) of the shell (10) has either an irregular quadrilateral or triangle cross-section with round corners. The height of the cylinder is from about 5 to about 6 cm. It is 5.5 cm for the preferred embodiment. There are circular openings (32) on its side-wall, which allow that the new bone from the nature femoral neck grows through. The openings could be round or elongated holes. The contours of the transverse cross-section of the cylinder (30) could be either quadrilateral or triangular shape with rounded corners (B—B and C—C in FIGS. 7 and 8) effective to be close to match the contours of the retention of the natural femoral neck. Such a design of the shell may have at least two functions. 1) It would hold the femoral neck tightly in order to enhance the strength of the neck bone. It is well known that the quality of neck bone might have been affected or damaged by disease. 2) It would prevent the rotation of the prosthesis. The longitudinal axis of the hollow cylinder would coincident with one of the natural femoral neck.

The foot section of the shell, a collar (40), radially extended from its cylindrical portion to the distal rim of the shell, has a hollow flared shape with a lower circumferential bone engaging surface that has varying concave to fit and to be secured to trochantic bed. Such a design of prosthesis allows that the shell fits tightly and precisely into the trochantic bed of the femur and directly conducts a compression force from prosthetic head into the trochantic bed of the femur as well as the cortical bone of the shaft. Typically, anterior shape of the flared collar (40) would be close to contact with the surface of the cliff-like anterior side of neck and shaft. The anterior and posterior rim of the shell present along the intertrochantic line and intertrochantic crest of proximal femur, respectively. Its lateral and medial shape of the collar would be more flat (less slopped) and cover the surface around the greater and lesser trochanter, respectively. There are circular openings or hole (41) on the collar wall in equal distance, at which the new bone can grow through them. It also allows the mechanical tools passes through for fastening the shell on the trochantic bed. The major advantage from such a design of the prosthesis is that most of the compression force from the prosthetic head would directly transmit into the trochantic bed as well as cortical bone of shaft through both prosthesis and the retention natural neck.

The hollow section of the shell has a wall thickness from about 1 to about 3-mm. The thickness of the preferred embodiment is locally varied to preferentially strength critical regions of the neck cylinder (30) and the collar (40).

In a more general embodiment, the inner surface of the shell has a coating materials which are preferably bonded to the bone for the biological fixation, such as bonding to either a microporous surface or to a surface-bound hydroxyapatite (HA) or other suitable bioactive material on the inner wall of the shell. This composition and method of application to the femoral prosthesis is taught, for example, in U.S. Pat. No. 4,550,448 (Kenna), which is incorporated herein by reference. The porous coating in designed to promote bone in-growth creates a bio-seal to prevent the migration of particulate debris.

Specially, the orientation of each part of the hollow shell may be precisely defined in three-dimensional space by a series of profiles, such as top, anterior (FIG. 1), medial plane (FIG. 2) and transverse projection (FIGS. 6, 7, 8 and 9) of the shell. For ease explanation, in all cases of following, we use the longitudinal axis of the shell and either the anterior or lateral plane as the reference to describe the orientation of each transverse sections of the shell, which are equally corresponding to the angle of inclination toward the longitudinal axis of the femoral shaft and the angle of anteversion toward the sagittal plane, respectively. There are X, Y and Z dimension, which represent the anterior plane with medial/lateral width, the medial plane with posterior/anterior width and B(bottom)-T(top) plane with bottom/top width of the left shell, respectively.

The inner shape of the hollow shell may be defined by, at least, four transverse cross sections depicted in FIG. 5, which corresponds to either each junction area between adjacent portion or the boundary of the shell. Those transverse cross sections of the shell may be defined by an angle toward the longitudinal axis of the shell in the defined plane (either anterior or medial plane). The configuration of the shell structure could be defined:

1) A—A cross section in FIG. 6, which depicts the upper end of the neck (20) of the shell, is a circle with a center hole. Its plane of the cross section is perpendicular (90 degrees) toward the longitudinal axis of the biological screw in both the anterior and medial planes.
2) B—B transverse cross section as described in FIG. 7, which is defined as the junction line between the lower part of the arcuate top portion or shoulder (31) and the upper part of the body cylinder(30), forms an angle from about 95 to about 105 degrees, most preferably about 100 degrees toward the longitudinal axis of the shell in the anterior plane and an angle from about 80 to about 90, most preferably about 85 degrees toward the longitudinal axis of the shell in the medial plane. The inside shape of B—B section here is a quadrilateral with round corners.
3) C—C transverse cross section, as described in FIG. 8, which represent the junction line between cylinder (30) and the collar (40) of the shell, forms an angle from about 75 to about 85 toward the longitudinal axis of the shell in the anterior plane of the shell and from about 70 to about 85 degrees toward the longitudinal axis of the shell in the medial plane of the shell. The inside shape of C—C section here is a quadrilateral with round corners.
4) D—D transverse cross section, as described in FIG. 9, represents the bottom shape of the collar (40), forms an angle of from about 95 to about 110 degrees toward the longitudinal axis of the shell in anterior plane of the shell and from about 92 to about 98 degrees toward the longitudinal axis of the shell in the medial plane of the shell.

The component of the inventive prosthesis may be fabricated from conventional bio-compatible materials or, such as a metal selected from the group consisting of either stainless steel, Cobalt-Chrome (Co—Cr) , Cobalt-Chrome-molybdenum (Co—Cr—Mo) and Titanium (Ti) alloys and ceramic, most preferably cobalt-chromium-molybdenum alloy.

The implantation and fixation of the prosthesis in present invention could comprise two procedures: a mechanically implantation of the prosthesis into the outside of the retention of the femoral neck and trochantic bed during operation and a biologically fixation between the prosthesis and bone surface.

The mechanical manner herein could be a nail, screw, pin and stem as well as any combination of them, which produces a primary anchorage of the shell onto the retention neck and natural trochantic bed. Such mechanical manners could be made of materials selected from the group comprising biocompatible materials and biodegradable materials.

The preferred embodiment in term of implantation of the shell is a combination of that a self-tapping screw or screw anchors the shell on the sculpted femoral neck and the trochantic bed through both bore (21) on the shell neck and that screws, pins or nails fasten the shell on the trochantic bed through openings on the collar wall (40) and neck cylinder (30), if necessary or desired.

Such a design of the prosthesis imbedded on outside of the sculpted femoral neck and trochantic bed leads that the hollow shell transmits primarily compressive force against both the neck and trochantic bed of the femur, as well as to the cortical bone of the shaft, particularly in the medial proximal shaft. That model is very close to one of force distribution on the natural proximal femur. The femoral prosthesis of the present invention is to function in the manner intended without loosening and without causing pain or other mechanical side effect in the patient.

The foregoing disclosure and description of the invention are illustrative and explanatory thereof, and various changes in the size, shape, materials and procedure, as well as in the details of the illustrated construction may be made without departing from the spirit of the invention.

We claim:

1. A prosthetic neck-locking femoral component for use in replacement of a defective hip joint, said femoral component comprising:

an asymmetric hollow neck-locking shell configured to encase and to be anchored to the outer surface of the femoral neck and the trochantic bed of the femur; and said shell including a proximal portion shaped to be inserted into a socket of an articulation component, a substantially hollow cylindrical portion adjacent to said proximal portion and sized to encase the out surface of the sculpted femoral neck and a collar extending radially outwardly from a distal rim of said shell for embedding into the outer surface of the trochantic bed, a screw for attaching said shell to the sculpted femoral neck and the trochantic bed.

2. The femoral component as set forth in claim 1, wherein said proximal portion includes a tapered cone for fitting into the socket of an articulation component, said a tapered cone having a longitudinal center, defining a logitudinal axis of said shell, said longitudinal axis forming a inclination angle with the famoral shaft of from about 120 to about 145 degrees and anteversion angle with a plane of the body from about 7 to about 15 degrees, if said component is implanted, said tapered cone having a bore oriented along said longitudinal axis of said shell said bore having a stage which is about 9-mm depth from the upper edge of the cone, for supporting said screw to attach said component to the femur.

3. The femoral component as set forth in claim 1, wherein said hollow cylindrical portion has varying cross section, along said longitudinal axis of said shell, forming a surface contour closely matching the outer surface of a sculpted femoral neck.

4. The femoral component as set forth in claim 1, wherein said collar includes a lower circumferential bone engaging surface that has a varying concave surface to fit and to be secured to the sculpted trochantic bed.

5. The femoral component as set forth in claim 1, wherein said shell contains openings, with varied shapes, in side-wall of said hollow cylinder portion and said collar for new bone growth there through.

6. The femoral component as set forth in claim 1, wherein said shell includes an inner bone engaging surface with either a porous coating or surface coating materials of hydroxyapatite (HA) and any bio-active coating materials on its inner surfaces of said shell for enhancing new bone growth into said bone engaging surface.

7. The femoral component as set forth in claim 1, wherein said shell is made of a biocompatible materials selected from the group consisting of stainless steel, Cobalt-Chrome(Co—Cr), Cobalt-Chrome-Molybdenum ( Co—Cr—Mo), Titanium (Ti) alloys and ceramics.

8. The femoral component as set forth in claim 1, wherein said screw is self-tapping screw, said self-tapping screw being insertable through said bore of said tapered cone, engaging with said stage of the inside of said bore further screwing into the shaft of femur and tightening said component into the sculpted trochantic bed of femur, said screw being made of materials selected from the group consisting of either biocompatible materials or biodegradable materials.

* * * * *